(12) United States Patent
Lange et al.

(10) Patent No.: US 6,476,060 B2
(45) Date of Patent: Nov. 5, 2002

(54) 4,5-DIHYDRO-1H-PYRAZOLE DERIVATIVES HAVING $CB_1$-ANTAGONISTIC ACTIVITY

(75) Inventors: Josephus H. M. Lange; Cornelis G. Kruse; Jacobus Tipker; Martinus T. M. Tulp; Bernard J. Van Vliet, all of Weesp (NL)

(73) Assignee: Solvay Pharmaceuticals, B.V. (NL)

( * ) Notice: Subject to any disclaimer, the term of this patent is extended or adjusted under 35 U.S.C. 154(b) by 19 days.

(21) Appl. No.: 09/814,694

(22) Filed: Mar. 23, 2001

(65) Prior Publication Data

US 2001/0053788 A1 Dec. 20, 2001

(30) Foreign Application Priority Data

Mar. 23, 2000 (EP) .............................................. 00201032
Mar. 23, 2000 (NL) .............................................. 1014728

(51) Int. Cl.[7] ........................ A61K 31/415; A61P 25/28; C07D 231/06
(52) U.S. Cl. ................. 514/403; 546/275.4; 548/365.7; 548/379.4; 548/379.7
(58) Field of Search ........................... 548/365.7, 379.4, 548/379.7; 546/275.4; 514/403

(56) References Cited

U.S. PATENT DOCUMENTS 5,591,764 A * 1/1997 Fahmy et al. ............ 548/379.4
5,624,941 A   4/1997 Barth et al.

* cited by examiner

Primary Examiner—Robert W. Ramsuer
(74) Attorney, Agent, or Firm—Finnegan, Henderson, Farabow, Garrett, & Dunner, L.L.P.

(57) ABSTRACT

The present invention relates, among many things, to novel 4,5-dihydro-1H-pyrazole compounds which can be potent antagonists of the cannabis $CB_1$-receptor.

The compounds have the formula (I)

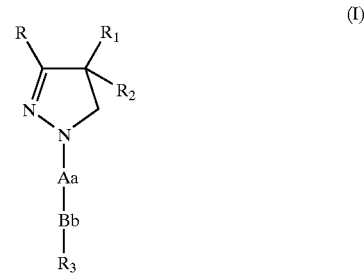

wherein

R and $R_1$ are the same or different and represent unsubstituted or substituted phenyl, thienyl, or pyridyl, or naphthyl. naphthyl $R_2$ represents hydrogen, hydroxy, $C_{1-3}$-alkoxy, acetyloxy or propionyloxy, Aa represents one of the groups (i), (ii), (iii), (iv) or (v) as defined herein, Bb represents sulfonyl or carbonyl, and $R_3$ represents benzyl, phenyl, thienyl or pyridyl, each of which is unsubstituted or substituted, or $R_3$ represents $C_{1-8}$ branched or unbranched alkyl or $C_{3-8}$ cycloalkyl, or $R_3$ represents naphthyl.

24 Claims, No Drawings

4,5-DIHYDRO-1H-PYRAZOLE DERIVATIVES HAVING $CB_1$-ANTAGONISTIC ACTIVITY

This application claims priority benefit under 35 U.S.C. § 119 of European patent application No. EP 00201032.0, filed Mar. 23, 2000, and Dutch patent application No. NL 1014728, filed Mar. 23, 2000, both of which are incorporated herein by reference.

The present invention relates, among many things, to a group of novel 4,5-dihydro-1H-pyrazole compounds, to methods for the preparation of these compounds, and to pharmaceutical compositions containing one or more of these compounds as an active component.

The above mentioned 4,5-dihydro-1H-pyrazoles can be potent Cannabis-1 ($CB_1$) receptor antagonists with utility for the treatment of psychiatric and neurological disorders.

Cannabinoids are present in the Indian hemp *Cannabis Sativa* L. and have been used as medicinal agents for centuries (Mechoulam, R.; Feigenbaum, J. J. *Prog. Med. Chem.* 1987, 24, 159). However, only within the past ten years the research in the cannabinoid area has revealed pivotal information on cannabinoid receptors and their (endogenous) agonists and antagonists. The discovery and the subsequent cloning of two different subtypes of Cannabinoid receptors ($CB_1$ and $CB_2$) stimulated the search for novel cannabinoid receptor antagonists (Munro, S.; Thomas, K. L.; Abu-Shaar, M. *Nature* 1993, 365, 61. Matsuda, L. A.; Bonner, T. I. *Cannabinoid Receptors*, Pertwee, R. G. Ed. 1995, 117, Academic Press, London). In addition, pharmaceutical companies became interested in the development of cannabinoid drugs for the treatment of diseases connected with disorders of the cannabinoid system. The wide distribution of $CB_1$ receptors in the brain, in combination with the strictly peripheral localization of the $CB_2$ receptor, makes the $CB_1$ receptor a very interesting molecular target for CNS-directed drug discovery in the areas of both psychiatric and neurological disorders (Consroe, P. *Neurobiology of Disease* 1998, 5, 534. Pop, E. *Curr. Opin. In CPNS Investigational Drugs* 1999, 1, 587. Greenberg, D. A. *Drug News Perspect.* 1999, 12, 458). Hitherto, three types of distinct $CB_1$ receptor antagonists are known. Sanofi disclosed their diarylpyrazole congeners as selective $CB_1$ receptor antagonists. A representative example is SR-141716A, which is currently undergoing Phase II clinical development for psychotic disorders (Dutta, A. K.; Sard, H.; Ryan, W.; Razdan, R. K.; Compton, D. R.; Martin, B. R. *Med. Chem. Res.* 1994, 5, 54. Lan, R.; Liu, Q.; Fan, P.; Lin, S.; Fernando, S. R.; McCallion, D.; Pertwee, R.; Makriyannis, A. *J. Med. Chem.* 1999, 42, 769. Nakamura-Palacios, E. M.; Moerschbaecher, J. M.; Barker, L. A. *CNS Drug Rev.* 1999, 5, 43). Aminoalkylindoles have been disclosed as $CB_1$ receptor antagonists. A representative example is Iodopravadoline (AM-630), which was introduced in 1995. AM-630 is a $CB_1$ receptor antagonist, but sometimes behaves as a weak partial agonist (Hosohata, K.; Quock, R. M.; Hosohata, Y.; Burkey, T. H.; Makriyannis, A.; Consroe, P.; Roeske, W. R.; Yamamura, H.I. *Life Sc.* 1997, 61, PL115). More recently, researchers from Eli Lilly described arylaroyl substituted benzofurans as selective $CB_1$ receptor antagonists (e.g., LY-320135) (Felder, C. C.; Joyce, K. E.; Briley, E. J.; Glass, M.; Mackie, K. P.; Fahey, K. J.; Cullinan, G. J.; Hunden, D. C.; Johnson, D. W.; Chaney, M. O.; Koppel, G. A.; Brownstein, M. *J. Pharmacol. Exp. Ther.* 1998, 284, 291). Recently, 3-alkyl-5,5'-diphenylimidazolidinediones were described as cannabinoid receptor ligands, which were indicated to be cannabinoid antagonists (Kanyonyo, M.; Govaerts, S. J.; Hermans, E.; Poupaert, J. H.; Lambert, D. M. *Biorg. Med.Chem. Lett.* 1999, 9, 2233). Interestingly, many $CB_1$ receptor antagonists have been reported to behave as inverse agonists in vitro (Landsman, R. S.; Burkey, T. H.; Consroe, P.; Roeske, W. R.; Yamamura, H. I. *Eur. J. Pharmacol.* 1997, 334, R1). Recent reviews provide a nice overview of the current status in the cannabinoid research area (Mechoulam, R.; Hanus, L.; Fride, E. *Prog. Med. Chem.* 1998, 35, 199. Lambert, D. M. *Curr. Med. Chem.* 1999, 6, 635. Mechoulam, R.; Fride, E.; Di Marzo, V. *Eur. J. Pharmacol.* 1998, 359, 1).

It has now surprisingly been found that the novel 4,5-dihydro-1H-pyrazole compounds of the formula (I), prodrugs thereof, tautomers thereof, stereoisomers thereof, and salts thereof

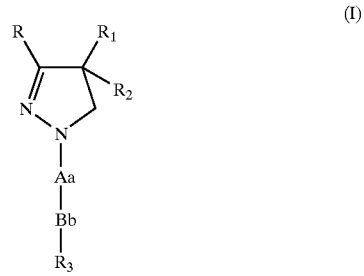

(I)

wherein

R represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl ($C_{1-2}$)-amino, dialkyl ($C_{1-2}$)-amino, monoalkyl ($C_{1-2}$)-amido, dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or R represents naphthyl, $R_1$ represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl ($C_{1-2}$)-amino, dialkyl ($C_{1-2}$)-amino, monoalkyl ($C_{1-2}$)-amido, dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or $R_1$ represents naphthyl, $R_2$ represents hydrogen, hydroxy, $C_{1-3}$-alkoxy, acetyloxy or propionyloxy, Aa represents one of the groups (i), (ii), (iii), (iv) or (v)

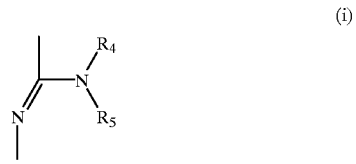

(i)

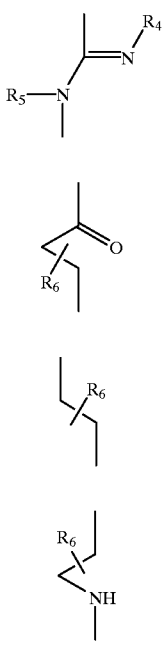

wherein
- $R_4$ represents hydrogen, $C_{1-8}$ branched or unbranched alkyl or $C_{3-8}$ cycloalkyl; and when $R_5$ represents hydrogen, $R_4$ optionally further represents acetamido, dimethylamino, 2,2,2-trifluoroethyl, phenyl or pyridyl,
- $R_5$ represents hydrogen, $C_{1-8}$ branched or unbranched alkyl or $C_{3-8}$ cycloalkyl,
- $R_6$ represents hydrogen or $C_{1-3}$ unbranched alkyl,
- Bb represents sulfonyl or carbonyl,
- $R_3$ represents benzyl, phenyl, thienyl or pyridyl, each of which is unsubstituted or substituted with 1, 2 or 3 substituents Y, which are the same or different, or $R_3$ represents $C_{1-8}$ branched or unbranched alkyl or $C_{3-8}$ cycloalkyl, or $R_3$ represents naphthyl, can be potent and/or selective antagonists of the cannabis $CB_1$-receptor.

Due to the potent $CB_1$ antagonistic activity possible, the compounds according to the invention can be suitable for use in the treatment of one or more psychiatric disorders such as psychosis, anxiety, depression, attention deficits, memory disorders and appetite disorders, obesity, neurological disorders such as dementia, distonia, Parkinson's disease, Alzheimer's disease, epilepsy, Huntington's disease, Tourette's syndrome, cerebral ischaemia, and/or for the treatment of pain disorders and/or other CNS-diseases such as those involving cannabinoid neurotransmission, and/or in the treatment of gastrointestinal disorders and/or cardiovascular disorders. Thus, the invention further relates to methods for treating a human or animal patient in need of such treating for one or more of these disorders. A method of treating according to the invention comprises administering a compound of formula (I) in an amount efficacious for the treating.

The affinity of representative compounds of the invention for cannabinoid $CB_1$ receptors was determined using membrane preparations of Chinese hamster ovary (CHO) cells in which the human cannabis $CB_1$ receptor is stably transfected in conjunction with [3H]CP-55,940 as radioligand. After incubation of a freshly prepared cell membrane preparation with the [3H]-ligand, with or without addition of compounds of the invention, separation of bound and free ligand was performed by filtration over glassfiber filters. Radioactivity on the filter was measured by liquid scintillation counting.

The cannabinoid $CB_1$ antagonistic activity of representative compounds of the invention was determined by functional studies using CHO cells in which human cannabinoid $CB_1$ receptors are stably expressed. Adenylyl cyclase was stimulated using forskolin and measured by quantifying the amount of accumulated cyclic AMP. Concomitant activation of $CB_1$ receptors by $CB_1$ receptor agonists (e.g., CP-55,940 or (R)-WIN-55,212-2) can attenuate the forskolin-induced accumulation of cAMP in a concentration-dependent manner. This $CB_1$ receptor-mediated response can be antagonised by $CB_1$ receptor antagonists such as by many of the compounds of the invention.

At least one center of chirality is present (at the $C_4$ position of the 4,5-dihydro-1H-pyrazole moiety) in the compounds of the formula (I). The invention relates both to racemates, mixtures of diastereomers, and the individual stereoisomers of the compounds having formula (I). The invention further relates both to the E isomer, Z isomer and E/Z mixtures of compounds having formula (I) wherein Aa has the meaning (i) or (ii) as described herein above.

Thus, "compound of formula (I)" and "compound having formula (I)" refer to any compound of formula (I), any prodrug thereof, any tautomer thereof, any stereoisomer thereof, and any salt thereof, unless indicated otherwise. One of ordinary skill in the art will recognize that E- and Z-isomers are a subset of, and are included within, "stereoisomers."

The compounds of the invention can be brought into forms suitable for administration by means of usual processes using auxiliary substances such as liquid or solid carrier materials. Thus, the invention also relates to compositions comprising at least one compound of formula (I) and at least one auxiliary substance. The invention also relates to methods for preparing a composition comprising mixing at least one compound of the formula (I) with at least one auxiliary substance. Many suitable auxiliary substances are readily known to those of ordinary skill in the art; care should be taken so that the selection of the at least one auxiliary substance will not, or will not substantially, adversely affect the desired properties of the composition.

If a composition according to the invention is intended for use in treating one or more of the disorders described above, then the composition may comprise at least one compound of formula (I) in an amount effective for the respective treating.

The invention also relates to processes for preparing a compound of formula (I).

The compounds of the invention having formula (III (vide infra), wherein $R_2$ represents hydrogen, can be obtained according to methods known, for example, those disclosed in EP 0021506 and DE 2529689, the disclosures of which are incorporated herein by reference.

A suitable synthesis for the compounds according to the present invention is the following:

Synthesis route A (for compounds having formula (I), wherein Aa has the meaning (i) or (ii) as described herein above).

In each of the following formulae, the radicals are as defined in formula (I), unless otherwise indicated.

Step 1 of route A

Reaction of a compound having formula (II)

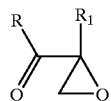
(II)

with hydrazine or hydrazine hydrate. This reaction gives a compound having formula (III)

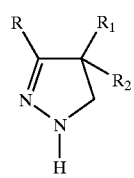
(III)

wherein $R_2$ represents a hydroxy group. This reaction, in some embodiments, is carried out in a polar solvent, such as, for example, ethanol. The invention also relates to novel compounds which can be intermediates in the preparation of compounds of formula (I). For example, compounds having formula (III) wherein $R_2$ represents a hydroxy group and wherein R and $R_1$ have the meaning as described herein above for compounds of formula (I) are new.

Step 2 of route A

Reaction of a compound having formula (III) with a compound having formula (IVa) or a compound having formula (IVb)

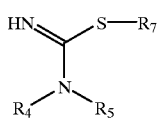
(IVa)

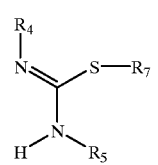
(IVb)

wherein $R_7$ represents a lower alkyl group, such as, for example, 2-methyl-2-thiopseudourea, or with a suitable salt form thereof in the presence of a base. In the present application, "lower alkyl group" means a straight, branched, or cyclic alkyl moiety having, for example, one to eight carbon atoms, which is unsubstituted or substituted by one or more radicals which do not substantially adversely affect the progress of the reaction. This reaction gives a 4,5-dihydro-1H-pyrazole-1-carboxamidine compound having formula (V)

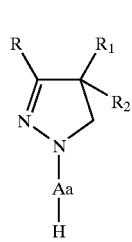
(V)

wherein Aa has the meaning (i) or (ii) as described herein above. Compounds having formula (V) wherein Aa has the meaning (i) or (ii) as described herein above and wherein R, $R_1$ and $R_2$ have the meaning as described herein above for compounds of the formula (I) are new.

Alternatively, a compound having formula (III) is reacted with a so-called guanylating agent. Examples of such guanylating agents are 1H-pyrazole-1-carboxamidine and its salts (for example the hydrochloride salt) and 3,5-dimethyl-1H-pyrazole-1-carboxamidine and its salts (for example the nitrate salt) and the like. This reaction gives a carboxamidine compound having formula (V).

Alternatively, a compound having formula (III) is reacted with a so-called protected guanylating agent. Examples of such protected guanylating agents are N-(benzyloxycarbonyl)-1H-pyrazole-1-carboxamidine, N-(tert-butoxycarbonyl)-1H-pyrazole-1-carboxamidine and N,N'-bis-(tert-butoxycarbonyl)-1H-pyrazole-1-carboxamidine and the like. This reaction gives, after deprotection, a compound having formula (V).

Step 3 of route A

The compound having formula (V) is reacted with an optionally substituted compound of the formula $R_3$-$SO_2$X or $R_3$-COX, wherein $R_3$ has the above mentioned meaning and X represents a halogen atom. This reaction, in some embodiments, is carried out in the presence of a base, such as triethylamine in an aprotic solvent, such as acetonitrile. This reaction gives a compounds of formula (I) wherein Bb represents a sulfonyl group or a carbonyl group, respectively.

Synthesis route A1 (for compounds having formula (I), wherein Aa has the meaning (i) or (ii) as described herein above)

Step 1 of route A1

Reaction of a compound having formula (III)

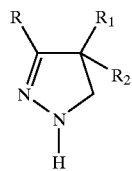
(III)

with a thioisocyanate compound having formula (VI).

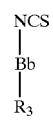
(VI)

This reaction, in some embodiments, is carried out in an inert organic solvent, such as for example acetonitrile. This reaction gives a thiocarboxamide compound having formula (VII). Compounds having formula (VII) wherein R, $R_1$, $R_2$, $R_3$ and Bb have the meanings as described herein above for compounds of formula (I) are new.

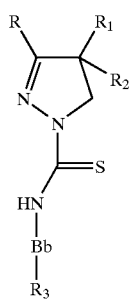

(VII)

Step 2 of route A1

Reaction of a compound having formula (VII) with an amine in the presence of a mercury(II) salt, such as for example $HgCl_2$, gives a compound having formula (I) wherein Aa has the meaning (i) or (ii) as described herein above. "Amine" refers to a nitrogen-containing species appropriately substituted with, for example $R_4$ and $R_5$ as defined above for the formula (I). The amine can be, for example, methylamine. This reaction, in some embodiments, is carried out in a polar organic solvent, such as, for example, acetonitrile.

Synthesis route A2 (for compounds having formula (I), wherein Aa has the meaning (i) or (ii) as described herein above)

Step 1 of route A2

Reaction of a compound having formula III

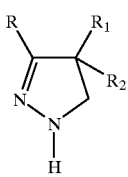

(III)

with a carbamate ester compound having formula (VIII).

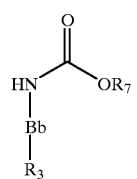

(VIII)

wherein $R_7$ represents a lower alkyl group, for example methyl. This reaction, in some embodiments, is carried out in an inert organic solvent, such as for example 1,4-dioxane. This reaction gives a 4,5-dihydropyrazole-1-carboxamide compound having formula (IX). Compounds having formula (IX) wherein R, $R_1$, $R_2$, $R_3$ and Bb have the meaning as described herein above for compounds of formula (I) are new.

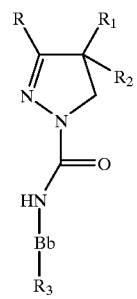

(IX)

Step 2 of route A2

Reaction of a compound having formula (IX) with a halogenating agent, such as for example $PCl_5$, gives a 4,5-dihydropyrazole-1-carboximidoyl halogenide compound having formula (X)

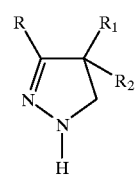

(X)

wherein $R_8$ represents a halogen atom, such as for example chloro. This reaction, in some embodiments, is carried out in an inert organic solvent, such as for example chlorobenzene.

Compounds having formula (X) wherein R, $R_1$, $R_2$, $R_3$ and Bb have the meaning as described herein above for compound (I) and wherein $R_8$ represents a halogen atom are new.

Step 3 of route A2

Reaction of a compound having formula (X) with an amine gives a compound having formula (I) wherein Aa has the meaning (i) or (ii) as described herein above.

This reaction, in some embodiments, is carried out in an inert organic solvent, such as for example dichloromethane.

Synthesis route A3 (for compounds having formula (I), wherein Aa has the meaning (i) or (ii) as described herein above)

Step 1 of route A3

Reaction of a compound having formula III (III)

with a dithioimidocarbonic ester compound having formula (XI).

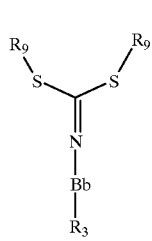

(XI)

wherein $R_9$ represents a $C_{1-3}$ alkyl group. This reaction, in some embodiments, is carried out in a polar organic solvent, such as for example acetonitrile. This reaction gives a carboximidothioic ester compound having formula (XII)

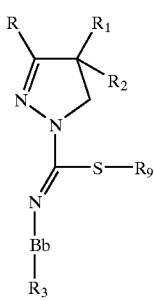

(XII)

wherein $R_9$ represents a $C_{1-3}$ alkyl group. Compounds having formula (XII) wherein R, $R_1$, $R_2$, $R_3$ and Bb have the meaning as described herein above for compounds of formula (I) and wherein $R_9$ represents a $C_{1-3}$ alkyl group are new.

Step 2 of route A3

Reaction of a compound having formula (XII) with an amine gives a compound having formula (I) wherein Aa has the meaning (i) or (ii) as described herein above.

This reaction, in some embodiments, is carried out in a polar organic solvent, such as, for example, methanol.

Synthesis route B (for compounds having formula (I), wherein Aa has the meaning (iii) or (iv) as described herein above)

Step 1 of route B

Reaction of a compound having formula (III)

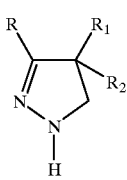

(III)

with a compound having formula (XIII), or a compound having formula (XIV), respectively

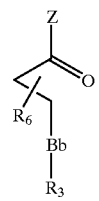

(XIII)

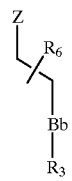

(XIV)

wherein Bb, $R_3$ and $R_6$ have the above mentioned meanings and Z represents a so-called leaving group. One of ordinary skill in the art will recognize suitable leaving groups, such as, for example, alkoxy radicals, halides, tosylates, triflates, and any moiety which tends to facilitate the reaction in the manner of a leaving group.

These reactions give compounds having formula (I), wherein Aa has the meaning (iii) or (iv), respectively.

Synthesis route C (for compounds having formula (I), wherein Aa has the meaning (v) as described herein above)

Step 1 of route C

Reaction of a compound having formula (III)

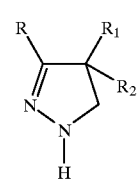

(III)

with an aziridine compound having formula (XV), or a compound having formula (XVI), respectively

(XV)

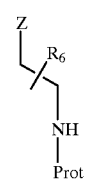

(XVI)

wherein $R_6$ has the above mentioned meaning, Z represents a so-called leaving group and Prot represents a so-called protective group, such as tert-butoxycarbonyl, benzyloxycarbonyl and the like.

These reactions give compounds having formula (XVII)

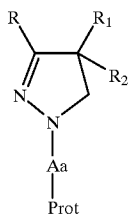

(XVII)

wherein Aa has the meaning (v) as described herein above. Compounds having formula (XVII) wherein R, $R_1$ and $R_2$ have the meaning as described herein above for compounds of formula (I) and wherein Aa has the meaning (v) as described herein above and wherein Prot represents a so-called protective group are new.

Subsequent removal of the so-called protective group according to known methods (see for example: T. W. Greene, P. G. M. Wuts, "Protective Groups in Organic Synthesis", third edition, John Wiley & Sons, Inc., New York, 1999) gives compounds of formula (V), wherein Aa has the meaning (v) as described herein above). Compounds having formula (V) wherein R, $R_1$ and $R_2$ have the meaning as described herein above for compounds of formula (I) and wherein Aa has the meaning (v) as described herein above are new.

Step 2 of route C

The compound having formula (V), wherein Aa has the meaning (v) as described herein above, is reacted with an optionally substituted compound of the formula $R_3$—$SO_2X$ or $R_3$—COX, wherein $R_3$ has the above mentioned meaning and X is halogen. This reaction, in some embodiments, is carried out in the presence of a base, such as triethylamine in an aprotic solvent, such as acetonitrile. This reaction gives compounds of formula (I) wherein Bb represents a sulfonyl group or carbonyl group respectively.

Alternatively, the above mentioned compound having formula (V) can be reacted with a compound of the formula $R_3$—COOH via formation of an active ester or in the presence of a so-called coupling reagent.

The preparation of representative compounds in accordance with the invention is illustrated in the following examples.

EXAMPLE I

3-(4-Chlorophenyl)-4,5-dihydro-4-hydroxy-4-phenyl-1H-pyrazole 2-(4-Chlorobenzoyl)-2-phenyloxirane (112 gram, 0.43 mol) was dissolved in ethanol (650 ml) at 35° C. To the resulting stirred solution was added $N_2H_4.H_2O$ (42 ml) and the formed 3-(4-chlorophenyl)-4,5-dihydro-4-hydroxy-4-phenyl-1H-pyrazole slowly precipitated. After standing for 16 hours the crystalline material was collected by filtration and successively washed with ethanol, water and ethanol and subsequently dried to give 3-(4-chlorophenyl)-4,5-dihydro-4-hydroxy-4-phenyl-1H-pyrazole (92 gram, 78% yield). Melting point: 195–196° C.

EXAMPLE II

3-(4-Chlorophenyl)-4,5-dihydro-N-((4-fluorophenyl)sulfonyl)-4-phenyl-1H-pyrazole-1-carboxamidine Part A: A stirred mixture of 3-(4-chlorophenyl)-4,5-dihydro-4-phenyl-1H-pyrazole (5.13 gram, 20.0 mmol), 2-methyl-2-thiopseudourea hydroiodide (5.00 gram, 23.0 mmol) and pyridine (10 ml) was heated at 110° C. for 1 hour. After one night standing at room temperature diethyl ether was added and the precipitate was collected by filtration. This precipitate was washed three times with diethyl ether portions to afford a solid (9 gram). Melting point: ~230° C. This solid was dissolved in methanol (20 ml). To the resulting solution was successively added a 2 N sodium hydroxide solution (12 ml) and water (200 ml). The formed precipitate was collected by filtration, washed two times with diethyl ether and successively with diisopropyl ether. The resulting solid was dried in vacuo to yield 3-(4-chlorophenyl)-4,5-dihydro-4-phenyl-1H-pyrazole-1-carboxamidine (5.1 gram, 88% yield). Melting point: 187–189° C.

Part B: To a stirred mixture of 3-(4-chlorophenyl)-4,5-dihydro-4-phenyl-1H-pyrazole-1-carboxamidine (0.50 gram, 1.68 mmol) and 4-fluorophenylsulfonyl chloride (0.34 gram, 1.75 mmol) in acetonitrile (10 ml) was added N,N-dimethyl-4-aminopyridine (0.020 gram, 0.175 mmol) and triethylamine (1 ml). The resulting solution was stirred at room temperature for 30 minutes. After addition of a 2 N sodium hydroxide solution and extraction with ethylacetate (400 ml), the ethylacetate layer was concentrated in vacuo. The resulting crude residue was further purified by means of flash chromatography (petroleum ether/diethyl ether=1/1 (v/v), followed by ethylacetate). Subsequent concentration in vacuo afforded solid 3-(4-chlorophenyl)-4,5-dihydro-N-((4-fluorophenyl)sulfonyl)-4-phenyl-1H-pyrazole-1-carboxamidine (0.55 gram, 72% yield). Melting point: 214–215° C.

In an analogous manner the compounds having formula (I) listed below have been prepared:

4,5-Dihydro-N-((4-fluorophenyl)sulfonyl)-3-(4-methoxyphenyl)-4-(4-methoxyphenyl)-1H-pyrazole-1-carboxamidine: Melting point: 155–156° C.

4,5-Dihydro-3-(4-methoxyphenyl)-4-(4-methoxyphenyl)-N-((4-methoxyphenyl)sulfonyl)-1H-pyrazole-1-carboxamidine: Melting point: 148–150° C.

3-(4-Chlorophenyl)-4,5-dihydro-4-phenyl-N-((2,4,6-trimethylphenyl)sulfonyl)-1H-pyrazole-1-carboxamidine: Melting point: 221–222° C.

3-(4-Chlorophenyl)-4,5-dihydro-N-((4-fluorophenyl)sulfonyl)-4-hydroxy-4-phenyl-1H-pyrazole-1-carboxamidine: Melting point: 227–228° C.

EXAMPLE III

3-(4-Chlorophenyl)-4,5-dihydro-N-(1-naphtoyl)-4-phenyl-1H-pyrazole-1-carboxamidine To a stirred mixture of 3-(4-chlorophenyl)-4,5-dihydro-4-phenyl-1H-pyrazole-1-carboxamidine (0.75 gram, 2.50 mmol) and 1-naphtoyl chloride (0.4 ml, 2.70 mmol) in acetonitrile (15 ml) was added triethylamine (1 ml). The resulting mixture was stirred at room temperature for 1 hour. After addition of a 2 N sodium hydroxide solution and extraction with ethylacetate, the ethylacetate layer was concentrated in vacua. The resulting crude residue was further purified by means of flash chromatography (petroleum ether/diethyl ether=3/1 (v/v), followed by ethylacetate). Subsequent concentration in vacuo afforded 3-(4-chlorophenyl)-4,5-dihydro-N-(1-naphtoyl)-4-phenyl-1H-pyrazole-1-carboxamidine (0.94 gram, 83% yield). Melting point: 206–207° C.

In an analogous manner the compound having formula (I) listed below has been prepared:

3-(4-Chlorophenyl)-4,5-dihydro-4-phenyl-N-(2-pyridoyl)-1H-pyrazole-1-carboxamidine. Melting point: 118° C. (decomposition).

EXAMPLE IV $N^1,N^1$-Dimethyl-$N^2$-((4-chlorophenyl)sulfonyl)-3-(4-chlorophenyl)-4,5-dihydro-4-phenyl-1H-pyrazole-1-carboxamidine Part A: A stirred mixture of 3-(4-chlorophenyl)-4,5-dihydro-4-phenyl-1H-pyrazole (12.0 gram, 46.8 mmol), [(4-chlorophenyl)sulfonyl]dithioimidocarbonic acid dimethyl ester (CAS: 13068-12-7) (9.20 gram, 31.1 mmol) and triethylamine (15 ml) in acetonitrile (200 ml) was heated at reflux temperature for 20 hours. An additional portion of 3-(4-chlorophenyl)-4,5-dihydro-4-phenyl-1H-pyrazole (12.0 gram, 46.8 mmol) was added and the resulting mixture was heated at reflux temperature for another 16 hours. After concentration in vacuo, dichloromethane was added and the resulting solution was washed twice with water and dried over anhydrous $Na_2SO_4$. After filtration and evaporation in vacuo the residue was further purified by flash chromatography (diethyl ether/petroleum ether=1/1 (v/v)) to give 3-(4-chlorophenyl)-N-((4-chlorophenyl)sulfonyl)-4,5-dihydro-4-phenyl-1H-pyrazole-1-carboximidothioic acid methyl ester (12.5 gram, 80% yield based on [(4-chlorophenyl)sulfonyl]dithioimidocarbonic acid dimethyl ester) as an amorphous solid.

Part B: To a stirred mixture of 3-(4-chlorophenyl)-N-((4-chlorophenyl)sulfonyl)-4,5-dihydro-4-phenyl-1H-pyrazole-1-carboximidothioic acid methyl ester (4.20 gram, 8.30 mmol) in methanol (75 ml) was added dimethylamine (10 ml) and dichloromethane (75 ml) and the resulting solution was stirred at room temperature for 6 hours. Evaporation in vacuo and subsequent flash chromatographic purification (diethyl ether/petroleum ether=1/1 (v/v), followed by diethyl ether) gave a solid which was further purified by recrystallisation from diisopropyl ether to yield $N^1,N^1$-dimethyl-$N^2$-((4-chloro-phenyl)sulfonyl)-3-(4-chlorophenyl)-4,5-dihydro-4-phenyl-1H-pyrazole-1-carboxamidine (2.63 gram, 63% yield). Melting point: 182° C.

In an analogous manner the compounds having formula (I) listed below have been prepared:

N-Methyl-N'-((4-chlorophenyl)sulfonyl)-3-(4-chlorophenyl)-4,5-dihydro-4-(3-pyridyl)-1H-pyrazole-1-carboxamidine. Melting point: 101–105° C.

N-Methyl-N'-((4-chlorophenyl)sulfonyl)-3-(4-chlorophenyl)-4,5-dihydro-4-(4-pyridyl)-1H-pyrazole-1-carboxamidine. Melting point: 112–115° C.

$N^1$, $N^1$-Dimethyl-$N^2$-((4-chlorophenyl)sulfonyl)-3-(4-chlorophenyl)-4,5-dihydro-4-hydroxy-4-phenyl-1H-pyrazole-1-carboxamidine. Melting point: Amorphous.

N-Ethyl-N'-((4-chlorophenyl)sulfonyl)-3-(4-chlorophenyl)-4,5-dihydro-4-hydroxy-4-phenyl-1H-pyrazole-1-carboxamidine. Melting point: 183–185° C.

EXAMPLE V

N-Methyl-N'-(3-(trifluoromethyl)benzoyl)-3-(4-chlorophenyl)-4,5-dihydro-4-phenyl-1H-pyrazole-1-carboxamidine Part A: To 3-(4-chlorophenyl)-4,5-dihydro-4-phenyl-1H-pyrazole (5.13 gram, 20.0 mmol) in acetonitrile (80 ml) was added 3-(trifluoromethyl)benzoylisothio-cyanate (4.62 gram, 20.0 mmol) at 0° C. and the resulting mixture was stirred for 1 hour. The formed yellow precipitate was collected by filtration and washed with a small portion of acetonitrile and water, respectively, and subsequently dried in vacuo to give 3-(4-chlorophenyl)-4,5-dihydro-4-phenyl-N-((3-trifluoromethyl)benzoyl)-1H-pyrazole-1-thiocarboxamide (8.26 gram, 85% yield). Melting point: 180–182° C.

Part B: To a stirred suspension of 3-(4-chlorophenyl)-4,5-dihydro-4-phenyl-N-((3-trifluoromethyl)benzoyl)-1H-pyrazole-1-thiocarboxamide (4.88 gram, 10.0 mmol) in acetonitrile (50 ml) was added cold methylamine (5 ml) to give a green solution. After addition of a solution of $HgCl_2$ (3.0 gram, 11 mmol) in 25 ml acetonitrile, the resulting mixture was stirred for three hours. The precipitate was removed by filtration over hyflo and the filtrate was collected and concentrated in vacuo. After addition of ethylacetate and 0.5 N NaOH, the ethylacetate layer was collected, washed with saturated aqueous NaCl solution and dried over anhydrous $Na_2SO_4$, filtered and concentrated in vacuo. Chromatography (dichloromethane/acetone=9/1 (v/v)) gave N-methyl-N'-(3-(trifluoro-methyl)benzoyl)-3-(4-chlorophenyl)-4,5-dihydro-4-phenyl-1H-pyrazole-1-carboxamidine (0.99 gram, 20% yield) as a foam. Melting point: Amorphous. $R_f$ (Silicagel: Dichloromethane/acetone= 9/1 (v/v))=0.3.

EXAMPLE VI

N-Methyl-N'-((4-chlorophenyl)sulfonyl)-3-(4-chlorophenyl)-4,5-dihydro-4-phenyl-1H-pyrazole-1-carboxamidine Part A: To a solution of N-((4-chlorophenyl)sulfonyl) carbamic acid methyl ester (CAS: 34543-04-9) (2.99 gram, 12.0 mmol) and pyridine (4 ml) in 1,4-dioxane (20 ml) was added 3-(4-chlorophenyl)-4,5-dihydro-4-phenyl-1H-pyrazole (3.39 gram, 13.2 mmol) and the resulting mixture was stirred for 4 hours at 100° C. After concentration in vacuo the residue was dissolved in dichloromethane, successively washed with water, 1 N HCl and water, dried over anhydrous $Na_2SO_4$, filtered and concentrated in vacuo to a volume of 20 ml. Methyl-tert-butyl ether (60 ml) was added and the resulting solution was concentrated to a volume of 20 ml. The formed crystals were collected by filtration and recrystallised from methyl-tert-butyl ether to give 3-(4-chlorophenyl)-N-((4-chlorophenyl)sulfonyl)-4,5-dihydro-4-phenyl-1H-pyrazole-1-carboxamide (4.75 gram, 76% yield). Melting point: 211–214° C.

Part B: A mixture of 3-(4-chlorophenyl)-N-((4-chlorophenyl)sulfonyl)-4,5-dihydro-4-phenyl-1H-pyrazole-1-carboxamide (3.67 gram, 7.75 mmol) and phosphorus pentachloride (1.69 gram, 8.14 mmol) in chlorobenzene (40 ml) was heated at reflux for 1 hour. After thorough concentration in vacuo, the formed N-((4-chlorophenyl)sulfonyl)-3-(4-chlorophenyl)-4,5-dihydro-4-phenyl-1H-pyrazole-1-carboximidoyl chloride was suspended in dichloromethane and reacted with cold methylamine (1.5 ml). After stirring at room temperature for 1 hour, the mixture was concentrated in vacuo. The residue was crystallised from diethyl ether to give N-methyl-N'-((4-chlorophenyl)sulfonyl)-3-(4-chlorophenyl)-4,5-dihydro-4-phenyl-1H-pyrazole-1-carboxamidine (2.29 gram, 61% yield). Melting point: 96–98° C. (dec.).

In an analogous manner the compounds having formula (I) listed below have been prepared:

N-Methyl-N'-((3-chlorophenyl)sulfonyl)-3-(4-chlorophenyl)-4,5-dihydro-4-phenyl-1H-pyrazole-1-carboxamidine. Melting point: 156–160° C.

N-Methyl-N'-((4-chlorophenyl)sulfonyl)-3-(5-chloro-2-thienyl)-4,5-dihydro-4-phenyl-1H-pyrazole-1-carboxamidine. Melting point: Amorphous.

N-Propyl-N'-((4-fluorophenyl)sulfonyl)-3-(4-chlorophenyl)-4,5-dihydro-4-phenyl-1H-pyrazole-1-carboxamidine. Melting point: 129–138° C.

N-(2-Propyl)-N'-((4-fluorophenyl)sulfonyl)-3-(4-chlorophenyl)-4,5-dihydro-4-phenyl-1H-pyrazole-1-carboxamidine. Melting point: 110–112° C.

N-Methyl-N'-((2-propyl)sulfonyl)-3-(4-chlorophenyl)-4,5-dihydro-4-phenyl-1H-pyrazole-1-carboxamidine. Melting point: Amorphous.

N-(2-Propyl)-N'-((4-chlorophenyl)sulfonyl)-3-(4-pyridyl)-4,5-dihydro-4-phenyl-1H-pyrazole-1-carboxamidine. Melting point: Amorphous.

$N^1$-Ethyl-$N^1$-methyl-$N^2$-((4-chlorophenyl)sulfonyl)-3-(4-chlorophenyl)-4,5-dihydro-4-phenyl-1H-pyrazole-1-carboxamidine. Melting point: 184° C.

$N^1$-Ethyl-$N^1$-methyl-$N^2$-((4-fluorophenyl)sulfonyl)-3-(4-chlorophenyl)-4,5-dihydro-4-phenyl-1H-pyrazole-1-carboxamidine. Melting point: 173–176° C.

$N^1,N^1$-Dimethyl-$N^2$-((4-(trifluoromethyl)phenyl)sulfonyl)-3-(4-chlorophenyl)-4,5-dihydro-4-phenyl-1H-pyrazole-1-carboxamidine. Melting point: 195–196° C.

$N^1,N^1$-Dimethyl-$N^2$-((3-methylphenyl)sulfonyl)-3-(4-chlorophenyl)-4,5-dihydro-4-phenyl-1H-pyrazole-1-carboxamidine. Melting point: 195–198° C.

$N^1,N^1$-Dimethyl-$N^2$-((3-methoxyphenyl)sulfonyl)-3-(4-chlorophenyl)-4,5-dihydro-4-phenyl-1H-pyrazole-1-carboxamidine. Melting point: 204–206° C.

N-Ethyl-N'-((4-chlorophenyl)sulfonyl)-3-(4-chlorophenyl)-4,5-dihydro-4-phenyl-1H-pyrazole-1-carboxamidine. Melting point: Amorphous.

N-Dimethylamino-N'-((4-chlorophenyl)sulfonyl)-3-(4-chlorophenyl)-4,5-dihydro-4-phenyl-1H-pyrazole-1-carboxamidine. Melting point: 155–159° C.

N-Methyl-N'-((4-(trifluoromethyl)phenyl)sulfonyl)-3-(4-chlorophenyl)-4,5-dihydro-4-phenyl-1H-pyrazole-1-carboxamidine. Melting point: Amorphous.

$N^1,N^1$-Dimethyl-$N^2$-((2-methylphenyl)sulfonyl)-3-(4-chlorophenyl)-4,5-dihydro-4-phenyl-1H-pyrazole-1-carboxamidine. Melting point: 148–151° C.

N-Methyl-N'-((2,4-difluorophenyl)sulfonyl)-3-(4-chlorophenyl)-4,5-dihydro-4-phenyl-1H-pyrazole-1-carboxamidine. Melting point: 85° C.

N-Acetamido-N'-((4-chlorophenyl)sulfonyl)-3-(4-chlorophenyl)-4,5-dihydro-4-phenyl-1H-pyrazole-1-carboxamidine. Melting point: Amorphous.

N-(2,2,2-Trifluoroethyl)-N'-((4-chlorophenyl)sulfonyl)-3-(4-chlorophenyl)-4,5-dihydro-4-phenyl-1H-pyrazole-1-carboxamidine. Melting point: Amorphous.

N-(2-Pyridyl)-N'-((4-chlorophenyl)sulfonyl)-3-(4-chlorophenyl)-4,5-dihydro-4-phenyl-1H-pyrazole-1-carboxamidine. Melting point: 142–146° C.

N-(4-Pyridyl)-N'-((4-chlorophenyl)sulfonyl)-3-(4-chlorophenyl)-4,5-dihydro-4-phenyl-1H-pyrazole-1-carboxamidine. Melting point: 204–206° C.

N-Phenyl-N'-((4-chlorophenyl)sulfonyl)-3-(4-chlorophenyl)-4,5-dihydro-4-phenyl-1H-pyrazole-1-carboxamidine. Melting point: 158–160° C.

EXAMPLE VII 3-(4-Chlorophenyl)-1-[3-((4-chlorophenyl)sulfonyl)butanoyl]-4,5-dihydro-4-phenyl-1H-pyrazole To a stirred mixture of 3-((4-chlorophenyl)sulfonyl)butyric acid (1.85 gram, 7.00 mmol), diisopropylethylamine (3 ml) and 1-ethyl-3-(3-dimethylaminopropyl)carbodiimide hydrochloride (1.50 gram, 15.7 mmol) was added 3-(4-chlorophenyl)-4-phenyl-4,5-dihydro-1H-pyrazole (3.00 gram, 11.7 mmol) and the resulting mixture was stirred for 16 hours at room temperature. After concentration in vacuo the resulting residue was purified by flash chromatography (petroleum ether/diethyl ether=1/2 (v/v), followed by diethyl ether) to give 3-(4-chlorophenyl)-1-[3-((4-chlorophenyl)sulfonyl)butanoyl]-4,5-dihydro-4-phenyl-1H-pyrazole (3.69 gram, 63% yield) as a diastereomeric mixture. Melting point: amorphous.

In an analogous manner the compounds having formula (I) listed below have been prepared:

3-(4-Chlorophenyl)-1-[3-(phenylsulfonyl)propanoyl]-4,5-dihydro-4-phenyl-1H-pyrazole. Melting point: 122–123° C.

3-(4-Chlorophenyl)-1-[3-((4-chlorophenyl)sulfonyl)propanoyl]-4,5-dihydro-4-phenyl-1H-pyrazole. Melting point: 178–181° C.

EXAMPLE VIII 3-(4-Chlorophenyl)-4,5-dihydro-4-phenyl-1-[2-((3-(trifluoromethyl)phenyl)-sulfonyl)ethyl]-1H-pyrazole To a stirred mixture of 3-(4-chlorophenyl)-4,5-dihydro-4-phenyl-1H-pyrazole (1.7 gram, 6.60 mmol) and collidine (2 ml) in acetonitrile (25 ml) was slowly added a solution of 2-((3-(trifluoromethyl)phenyl)sulfonyl)ethyl chloride (1.5 gram, 5.50 mmol) in acetonitrile (20 ml) and the resulting solution was heated at reflux temperature for 16 hours. After concentration in vacuo the residue was dissolved in ethylacetate and washed with aqueous sodium hydrogencarbonate solution. The resulting ethylacetate layer was successively washed with 1 N hydrochloric acid solution and aqueous sodium hydrogencarbonate solution. Subsequent flash chromatographic purification (petroleum ether/diethyl ether=1/2 (v/v)) gave an oil which was crystallised from diisopropyl ether to afford 3-(4-chlorophenyl)-4,5-dihydro-4-phenyl-1-[2-((3-(trifluoromethyl)phenyl)sulfonyl)ethyl]-1H-pyrazole (0.52 gram, 19% yield). Melting point: 118–119° C.

In an analogous manner the compounds having formula (I) listed below have been prepared:

3-(4-Chlorophenyl)-1-[2-(benzylsulfonyl)ethyl]-4,5-dihydro-4-phenyl-1H-pyrazole. Melting point: 161° C.

3-(4-Chlorophenyl)-1-[2-((4-chlorophenyl)sulfonyl)ethyl]-4,5-dihydro-4-phenyl-1H-pyrazole. Melting point: Amorphous.

3-(4-Chlorophenyl)-1-[2-((4-chlorophenyl)sulfonyl)ethyl]-4,5-dihydro-4-hydroxy-4-phenyl-1H-pyrazole. Melting point: 127–128° C.

EXAMPLE IX

N-[2-(3-(4-Chlorophenyl)-4,5-dihydro-4-phenyl-1H-pyrazol-1-yl)ethyl]-3-(trifluoromethyl)benzenesulfonamide Part A: A stirred solution of 3-(4-chlorophenyl)-4,5-dihydro-4-phenyl-1H-pyrazole (5.00 gram, 19.5 mmol) and N-(tert-butoxycarbonyl)aziridine (2.00 gram, 14.0 mmol) in toluene (100 ml) was heated at reflux temperature for 16 hours. After concentration in vacuo the residue was purified by flash chromatography (petroleum ether/diethyl ether=3/1 (v/v)), followed by petroleum ether/diethyl ether=1/1 (v/v)).

After concentration in vacuo the remaining oily residue was crystallised from diisopropyl ether to afford 1-[2-((tert-butoxycarbonyl)amino)ethyl]-3-(4-chlorophenyl)-4,5-dihydro-4-phenyl-1H-pyrazole (1.91 gram, 34%). Repeated crystallisations from the mother liquor afforded an additional amount of crystalline 1-[2-((tert-butoxycarbonyl)amino)ethyl]-3-(4-chlorophenyl)-4,5-dihydro-4-phenyl-1H-pyrazole (1.19 gram).

Part B: To a solution of 1-[2-((tert-butoxycarbonyl)amino)ethyl]-3-(4-chlorophenyl)-4,5-dihydro-4-phenyl-1H-pyrazole (1.91 gram, 4.8 mmol) in dichloromethane (50 ml) was added trifluoroacetic acid (5 ml) and the resulting solution was stirred at room temperature for 5 hours. After concentration in vacuo the residue was dissolved in ethylacetate and washed with 2 N sodium hydroxide solution. The ethyl acetate layer was dried over magnesium sulfate, filtered and concentrated in vacuo to afford 1-(2-aminoethyl)-3-(4-chlorophenyl)-4,5-dihydro-4-phenyl-1H-pyrazole (1.44 gram, quantitative yield) as an oil.

Part C: To a solution of 1-(2-aminoethyl)-3-(4-chlorophenyl)-4,5-dihydro-4-phenyl-1H-pyrazole (0.56 gram, 1.87 mmol) and diisopropylethylamine in acetonitrile (20 ml) was added 3-(trifluoromethyl)phenylsulfonyl chloride (0.35 ml, 2.18 mmol) and the resulting solution was stirred at room temperature for 20 minutes. After concentration in vacuo the residue was dissolved in ethylacetate and washed with 2 N sodium hydroxide solution. The ethylacetate layer was concentrated in vacuo. The resulting oil was crystallised from a small amount of diisopropyl ether to afford crystalline N-[2-(3-(4-chlorophenyl)-4,5-dihydro-4-phenyl-1H-pyrazol-1-yl)ethyl]-3-(trifluoromethyl)benzenesulfonamide (0.44 gram, 46% yield). Melting point: 94–96° C.

EXAMPLE X (−)-N-methyl-N'-((4-chlorophenyl)sulfonyl)-3-(4-chlorophenyl)-4,5-dihydro-4-phenyl-1H-pyrazole-1-carboxamidine (−)-N-Methyl-N'-((4-chlorophenyl)sulfonyl)-3-(4-chlorophenyl)-4,5-dihydro-4-phenyl-1H-pyrazole-1-carboxamidine (7.16 gram, 0.0147 mol)) ($[\alpha^{25}_D]=-150°$, c=0.01, MeOH) (melting point: 169–170° C.) was obtained via chiral chromatographic separation of racemic N-methyl-N'-((4-chlorophenyl)sulfonyl)-3-(4-chlorophenyl)-4,5-dihydro-4-phenyl-1H-pyrazole-1-carboxamidine (18 gram, 0.037 mol) using a Chiralpak AD, 20 μm chiral stationary phase. The mobile phase consisted of a mixture of hexane/ethanol (80/20 (v/v)) and 0.1% ammonium hydroxide (25% aqueous solution).

In an analogous manner the optically pure compounds listed below have been prepared from the corresponding racemates:

(−)-N-Ethyl-N'-((4-chlorophenyl)sulfonyl)-3-(4-chlorophenyl)-4,5-dihydro-4-phenyl-1H-pyrazole-1-carboxamidine: ($[\alpha^{25}_D]=-126°$, c=0.01, CHCl$_3$); Melting point: 172–175° C. Stationary phase: Chiralcel OD. Mobile phase: A mixture of heptane/2-propanol (85/15 (v/v)).

(−)-N-Dimethylamino-N'-((4-chlorophenyl)sulfonyl)-3-(4-chlorophenyl)-4,5-dihydro-4-phenyl-1H-pyrazole-1-carboxamidine: ($[\alpha^{25}_D]=-132°$, c=0.01, CHCl$_3$); Melting point: 218–224° C. Stationary phase: Chiralcel OD. Mobile phase: A mixture of heptane/2-propanol (85/15 (v/v)).

(−)-N-Methyl-N'-((4-(trifluoromethyl)phenyl)sulfonyl)-3-(4-chlorophenyl)-4,5-dihydro-4-phenyl-1H-pyrazole-1-carboxamidine: ($[\alpha^{25}_D]=-131°$, c=0.01, CHCl$_3$); Melting point: 157–160° C. Stationary phase: Chiralcel OD. Mobile phase: A mixture of heptane/2-propanol (85/15 (v/v)).

(−)-N$^1$,N$^1$-Dimethyl-N$^2$-((2-methylphenyl)sulfonyl)-3-(4-chlorophenyl)-4,5-dihydro-4-phenyl-1H-pyrazole-1-carboxamidine: ($[\alpha^{25}_D]=-88°$, c=0.01, MeOH); Melting point: Amorphous. Stationary phase: Chiralpak AD. Mobile phase: Ethanol.

(−)-N-Methyl-N'-((2,4-difluorophenyl)sulfonyl)-3-(4-chlorophenyl)-4,5-dihydro-4-phenyl-1H-pyrazole-1-carboxamidine: ($[\alpha^{25}_D]=-129°$, c=0.01, MeOH); Melting point: Amorphous. Chiralpak AD. Mobile phase: Methanol.

We claim:

1. A compound of formula (I)

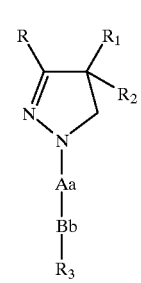

(I)

wherein

R represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl ($C_{1-2}$)-amino, dialkyl ($C_{1-2}$)-amino, monoalkyl ($C_{1-2}$)-amido, dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or R represents naphthyl, $R_1$ represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl ($C_{1-2}$)-amino, dialkyl ($C_{1-2}$)-amino, monoalkyl ($C_{1-2}$)-amido, dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or $R_1$ represents naphthyl, $R_2$ represents hydrogen, hydroxy, $C_{1-3}$-alkoxy, acetyloxy or propionyloxy, Aa represents one of groups (i), (ii), (iii), (iv) or (v)

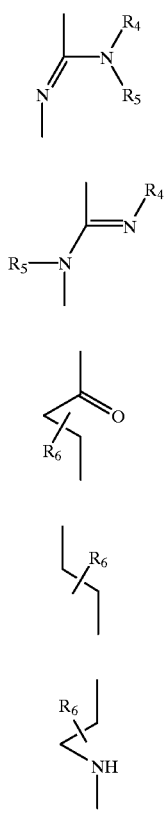

wherein
- $R_4$ represents hydrogen, $C_{1-8}$ branched or unbranched alkyl or $C_{3-8}$ cycloalkyl; and when $R_5$ represents hydrogen, $R_4$ optionally further represents acetamido, dimethylamino, 2,2,2-trifluoroethyl, phenyl or pyridyl,
- $R_5$ represents hydrogen, $C_{1-8}$ branched or unbranched alkyl or $C_{3-8}$ cycloalkyl,
- $R_6$ represents hydrogen or $C_{1-3}$ unbranched alkyl,
- Bb represents sulfonyl or carbonyl,
- $R_3$ represents benzyl, phenyl, thienyl or pyridyl, each of which is unsubstituted or substituted with 1, 2 or 3 substituents Y, which are the same or different, or $R_3$ represents $C_{1-8}$ branched or unbranched alkyl or $C_{3-8}$ cycloalkyl, or $R_3$ represents naphthyl.

2. The compound of formula (I) as claimed in claim 1, wherein the compound is a prodrug thereof, a tautomer thereof, a stereoisomer thereof, or a salt thereof.

3. The compound of formula (I) as claimed in claim 1, wherein R is 4-chlorophenyl, $R_1$ is phenyl, $R_2$ is hydrogen, Aa is the group (i) wherein $R_4$ is hydrogen and $R_5$ is methyl, Bb is sulfonyl, and $R_3$ is 4-chlorophenyl.

4. The compound of formula (I) as claimed in claim 3, wherein the compound is a levorotatory enantiomer.

5. A composition comprising at least one compound of formula (I) as claimed in claim 1, and at least one auxiliary substance.

6. The composition as claimed in claim 5, wherein the at least one compound of formula (I) is present in an amount effective for treating a psychiatric disorder, a gastrointestinal disorder, a cardiovascular disorder, or a combination of said disorders, in a human or animal patient in need of such treating.

7. A method of preparing a composition comprising mixing at least one compound of formula (I) as claimed in claim 1, and at least one auxiliary substance.

8. A process for preparing a compound of formula (I) as claimed in claim 1, wherein Aa is the group (i) or (ii), the process comprising:

1) reacting a compound having formula (II)

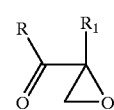

wherein R and $R_1$ are as defined for the compound of formula (I),
with hydrazine, hydrazine hydrate, or a mixture thereof, to obtain a compound having formula (III),

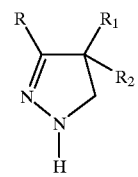

wherein R, $R_1$, and $R_2$ are as defined for the compound of formula (I), reacting the compound having formula (III) with a compound having formula (IVa) or (IVb)

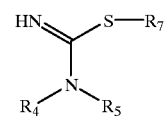

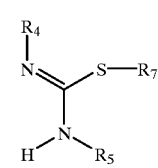

wherein $R_4$ and $R_5$ are as defined for the compound of formula (I), and $R_7$ represents a lower alkyl group,
to obtain a compound having formula (V),

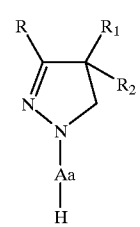

wherein R, $R_1$, $R_2$ and Aa are as defined for the compound of formula (I), and
reacting the compound having formula (V) with a compound of the formula $R_3\text{-}SO_2X$ or $R_3\text{-}COX$, wherein X is halogen and $R_3$ is as defined for the compound of formula (I), to yield the compound of formula (I);

or 2) reacting a compound having formula (III)

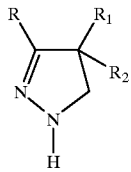
(III)

wherein R, $R_1$, and $R_2$ are as defined for the compound of formula (I), with a thioisocyanate compound having formula (VI)

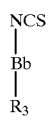
(VI)

wherein Bb and $R_3$ are as defined for the compound of formula (I), to obtain a compound of the formula (VII),

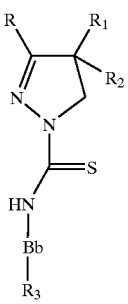
(VII)

wherein R, $R_1$, $R_2$, Bb, and $R_3$ are as defined for the compound of formula (I), reacting the compound of the formula (VII) with an amine in the presence of a mercury (II) salt, to yield the compound of formula (I);

or 3) reacting a compound having formula (III)

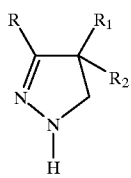
(III)

wherein R, $R_1$, and $R_2$ are as defined for the compound of formula (I), with a compound of the formula (VIII)

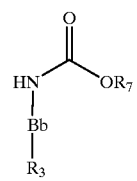
(VIII)

wherein Bb and $R_3$ are as defined for the compound of formula (I), and $R_7$ is a lower alkyl group, to give a compound of the formula (IX)

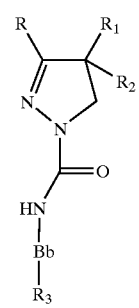
(IX)

wherein R, $R_1$, $R_2$, Bb, and $R_3$ are as defined for the compound of formula (I), reacting the compound of the formula (IX) with a halogenating agent to give a compound having formula (X)

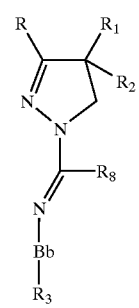
(X)

wherein R, $R_1$, $R_2$, Bb, and $R_3$ are as defined for the compound of formula (I), and $R_8$ is a halogen atom, and reacting the compound having formula (X) with an amine, to yield the compound of formula (I);

or 4) reacting a compound having formula (III)

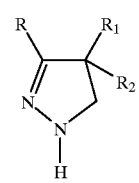
(III)

wherein R, $R_1$, and $R_2$ are as defined for the compound of formula (I), with a compound of the formula (XI)

(XI)

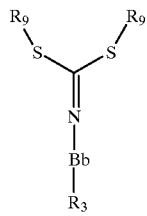

wherein Bb and $R_3$ are as defined for the compound of formula (I), and $R_9$ is a $C_{1-3}$ alkyl group, to give a compound having formula (XII)

(XII)

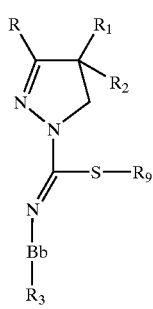

wherein R, $R_1$, $R_2$, Bb, and $R_3$ are as defined for the compound of formula (I), and $R_9$ is a $C_{1-3}$ alkyl group, and reacting the compound having formula (XII) with an amine, to yield the compound of formula (I).

9. A process for preparing a compound of formula (I) as claimed in claim 1, wherein Aa is the group (iii) or (iv), the process comprising:

reacting a compound of the formula (III)

(III)

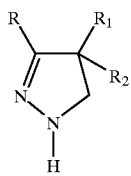

wherein R, $R_1$, and $R_2$ are as defined for the compound of formula (I), with a compound of the formula (XIII) or with a compound of the formula (XIV), (XIII)

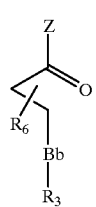

-continued (XIV)

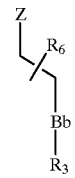

wherein Bb, $R_3$ and $R_6$ are as defined for the compound of formula (I), and Z is a leaving group, to yield the compound of formula (I).

10. A process for preparing a compound of formula (I) as claimed in claim 1, wherein Aa is the group (v), the process comprising:

reacting a compound having formula (III)

(III)

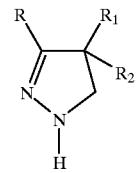

wherein R, $R_1$, and $R_2$ are as defined for the compound of formula (I), with a compound having formula (XV) or (XVI)

(XV)

(XVI)

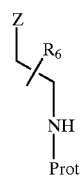

wherein $R_6$ is as defined for the compound of formula (I), Z is a leaving group, and Prot is a protective group, to give a compound having formula (XVII), (XVII)

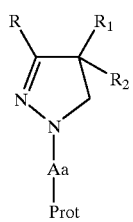

wherein R, $R_1$, $R_2$, and Aa are as defined for the compound of formula (I), and Prot is a protective group, deprotecting the compound having formula (XVII) to give a compound having formula (V),

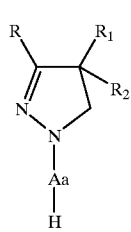
(V)

wherein R, R$_1$, R$_2$, and Aa are as defined for the compound of formula (I), and reacting the compound having formula (V) with a compound having formula R$_3$—SO$_2$X or R$_3$—COX wherein X is halogen or with a compound of the formula R$_3$—COOH, wherein R$_3$ in each of the foregoing formulae are as defined for the compound of formula (I), to yield the compound of formula (I).

11. A compound of formula (III), or a tautomer, a stereoisomer, or a salt thereof:

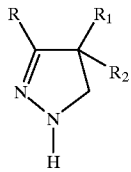
(III)

wherein R$_2$ represents a hydroxy group,

R represents phenyl, thienyl or pyridyl, each of which is unsubstituted or substituted with 1, 2 or 3 substituents Y, which are the same or different and are chosen from C$_{1-3}$-alkyl, C$_{1-3}$-alkoxy, hydroxy, halogen, trifluoromethyl, trifluoromethylthio, trifluoromethoxy, nitro, amino, monoalkyl (C$_{1-2}$)-amino, dialkyl (C$_{1-2}$)-amino, monoalkyl (C$_{1-2}$)-amido, dialkyl (C$_{1-2}$)-amido, (C$_{1-3}$)-alkyl sulfonyl, dimethylsulfamido, C$_{1-3}$-alkoxycarbonyl, carboxyl, trifluoromethylsulfonyl, cyano, carbamoyl, sulfamoyl and acetyl, or R represents naphthyl, and R$_1$ represents phenyl, thienyl or pyridyl, each of which is unsubstituted or substituted with 1, 2 or 3 substituents Y, which are the same or different and are chosen from C$_{1-3}$-alkyl, C$_{1-3}$-alkoxy, hydroxy, halogen, trifluoromethyl, trifluoromethylthio, trifluoromethoxy, nitro, amino, monoalkyl (C$_{1-2}$)-amino, dialkyl (C$_{1-2}$)-amino, monoalkyl (C$_{1-2}$)-amido, dialkyl (C$_{1-2}$)-amido, (C$_{1-3}$)-alkyl sulfonyl, dimethylsulfamido, C$_{1-3}$-alkoxycarbonyl, carboxyl, trifluoromethylsulfonyl, cyano, carbamoyl, sulfamoyl and acetyl, or R$_1$ represents naphthyl.

12. A compound of formula (V), or a tautomer, a stereoisomer, or a salt thereof:

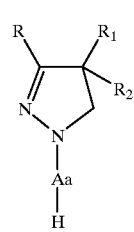
(V)

wherein

Aa represents one of groups (i), (ii), or (v)

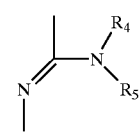
(i)

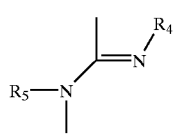
(ii)

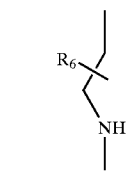
(v)

wherein

R$_4$ represents hydrogen, C$_{1-8}$ branched or unbranched alkyl or C$_{3-8}$ cycloalkyl; and when R$_5$ represents hydrogen, R$_4$ optionally further represents acetamido, dimethylamino, 2,2,2-trifluoroethyl, phenyl or pyridyl, R$_5$ represents hydrogen, C$_{1-8}$ branched or unbranched alkyl or C$_{3-8}$ cycloalkyl, R$_6$ represents hydrogen or C$_{1-3}$ unbranched alkyl, R represents phenyl, thienyl or pyridyl, each of which is unsubstituted or substituted with 1, 2 or 3 substituents Y, which are the same or different and are chosen from C$_{1-3}$-alkyl, C$_{1-3}$-alkoxy, hydroxy, halogen, trifluoromethyl, trifluoromethylthio, trifluoromethoxy, nitro, amino, monoalkyl (C$_{1-2}$)-amino, dialkyl (C$_{1-2}$)-amino, monoalkyl (C$_{1-2}$)-amido, dialkyl (C$_{1-2}$)-amido, (C$_{1-3}$)-alkyl sulfonyl, dimethylsulfamido, C$_{1-3}$-alkoxycarbonyl, carboxyl, trifluoromethylsulfonyl, cyano, carbamoyl, sulfamoyl and acetyl, or R represents naphthyl, R$_1$ represents phenyl, thienyl or pyridyl, each of which is unsubstituted or substituted with 1, 2 or 3 substituents Y, which are the same or different and are chosen from C$_{1-3}$-alkyl, C$_{1-3}$-alkoxy, hydroxy, halogen, trifluoromethyl, trifluoromethylthio, trifluoromethoxy, nitro, amino, monoalkyl (C$_{1-2}$)-amino, dialkyl (C$_{1-2}$)-amino, monoalkyl (C$_{1-2}$)-amido, dialkyl (C$_{1-2}$)-amido, (C$_{1-3}$)-alkyl sulfonyl, dimethylsulfamido, C$_{1-3}$-alkoxycarbonyl, carboxyl, trifluoromethylsulfonyl, cyano, carbamoyl, sulfamoyl and acetyl, or R₁ represents naphthyl, and R₂ represents hydrogen, hydroxy, $C_{1-3}$-alkoxy, acetyloxy or propionyloxy.

13. A compound of formula (VII), or a tautomer, a stereoisomer, or a salt thereof:

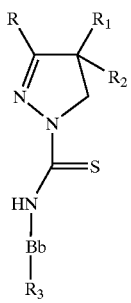

(VII)

wherein

R represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl ($C_{1-2}$)-amino, dialkyl ($C_{1-2}$)-amino, monoalkyl ($C_{1-2}$)-amido, dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or R represents naphthyl, R₁ represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl ($C_{1-2}$)-amino, dialkyl ($C_{1-2}$)-amino, monoalkyl ($C_{1-2}$)-amido, dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or R₁ represents naphthyl, R₂ represents hydrogen, hydroxy, $C_{1-3}$-alkoxy, acetyloxy or propionyloxy, R₃ represents benzyl, phenyl, thienyl or pyridyl, each of which is unsubstituted or substituted with 1, 2 or 3 substituents Y, which are the same or different, or R₃ represents $C_{1-8}$ branched or unbranched alkyl or $C_{3-8}$ cycloalkyl, or R₃ represents naphthyl, and Bb represents sulfonyl or carbonyl.

14. A compound of formula (IX), or a tautomer, a stereoisomer, or a salt thereof:

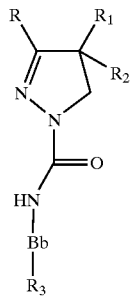

(IX)

wherein

R represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl ($C_{1-2}$)-amino, dialkyl ($C_{1-2}$)-amino, monoalkyl ($C_{1-2}$)-amido, dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or R represents naphthyl, R₁ represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl ($C_{1-2}$)-amino, dialkyl ($C_{1-2}$)-amino, monoalkyl ($C_{1-2}$)-amido, dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or R₁ represents naphthyl, R₂ represents hydrogen, hydroxy, $C_{1-3}$-alkoxy, acetyloxy or propionyloxy, R₃ represents benzyl, phenyl, thienyl or pyridyl, each of which is unsubstituted or substituted with 1, 2 or 3 substituents Y, which are the same or different, or R₃ represents $C_{1-8}$ branched or unbranched alkyl or $C_{3-8}$ cycloalkyl, or R₃ represents naphthyl, and Bb represents sulfonyl or carbonyl.

15. A compound of formula (X), or a tautomer, a stereoisomer, or a salt thereof:

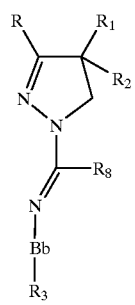

(X)

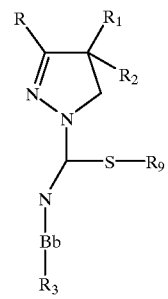

(XII)

wherein

R represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl $(C_{1-2})$-amino, dialkyl $(C_{1-2})$-amino, monoalkyl $(C_{1-2})$-amido, dialkyl $(C_{1-2})$-amido, $(C_{1-3})$-alkyl sulfonyl, dimethylsulfamido, $C_{1-3}$-alkoxycarbonyl, carboxyl, trifluoromethylsulfonyl, cyano, carbamoyl, sulfamoyl and acetyl, or R represents naphthyl, $R_1$ represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl $(C_{1-2})$-amino, dialkyl $(C_{1-2})$-amino, monoalkyl $(C_{1-2})$-amido, dialkyl $(C_{1-2})$-amido, $(C_{1-3})$-alkyl sulfonyl, dimethylsulfamido, $C_{1-3}$-alkoxycarbonyl, carboxyl, trifluoromethylsulfonyl, cyano, carbamoyl, sulfamoyl and acetyl, or $R_1$ represents naphthyl, $R_2$ represents hydrogen, hydroxy, $C_{1-3}$-alkoxy, acetyloxy or propionyloxy, $R_3$ represents benzyl, phenyl, thienyl or pyridyl, each of which is unsubstituted or substituted with 1, 2 or 3 substituents Y, which are the same or different, or $R_3$ represents $C_{1-8}$ branched or unbranched alkyl or $C_{3-8}$ cycloalkyl, or $R_3$ represents naphthyl, Bb represents sulfonyl or carbonyl, and $R_8$ represents a halogen atom.

16. A compound of formula (XII), or a tautomer, a stereoisomer, or a salt thereof:

wherein

R represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl $(C_{1-2})$-amino, dialkyl $(C_{1-2})$-amino, monoalkyl $(C_{1-2})$-amido, dialkyl $(C_{1-2})$-amido, $(C_{1-3})$-alkyl sulfonyl, dimethylsulfamido, $C_{1-3}$-alkoxycarbonyl, carboxyl, trifluoromethylsulfonyl, cyano, carbamoyl, sulfamoyl and acetyl, or R represents naphthyl, $R_1$ represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl $(C_{1-2})$-amino, dialkyl $(C_{1-2})$-amino, monoalkyl $(C_{1-2})$-amido, dialkyl $(C_{1-2})$-amido, $(C_{1-3})$-alkyl sulfonyl, dimethylsulfamido, $C_{1-3}$-alkoxycarbonyl, carboxyl, trifluoromethylsulfonyl, cyano, carbamoyl, sulfamoyl and acetyl, or $R_1$ represents naphthyl, $R_2$ represents hydrogen, hydroxy, $C_{1-3}$-alkoxy, acetyloxy or propionyloxy, $R_3$ represents benzyl, phenyl, thienyl or pyridyl, each of which is unsubstituted or substituted with 1, 2 or 3 substituents Y, which are the same or different, or $R_3$ represents $C_{1-8}$ branched or unbranched alkyl or $C_{3-8}$ cycloalkyl, or $R_3$ represents naphthyl, Bb represents sulfonyl or carbonyl, and $R_9$ represents a $C_{1-3}$ alkyl group.

17. A compound of formula (XVII), or a tautomer, a stereoisomer, or a salt thereof:

(XVII)

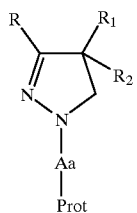

wherein

R represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl ($C_{1-2}$)-amino, dialkyl ($C_{1-2}$)-amino, monoalkyl ($C_{1-2}$)-amido, dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or R represents naphthyl, $R_1$ represents phenyl, thienyl or pyridyl, each of which is unsubstituted or substituted with 1, 2 or 3 substituents Y, which are the same or different and are chosen from $C_{1-3}$-alkyl, $C_{1-3}$-alkoxy, hydroxy, halogen, trifluoromethyl, trifluoromethylthio, trifluoromethoxy, nitro, amino, monoalkyl ($C_{1-2}$)-amino, dialkyl ($C_{1-2}$)-amino, monoalkyl ($C_{1-2}$)-amido, dialkyl ($C_{1-2}$)-amido, ($C_{1-3}$)-alkyl sulfonyl, dimethylsulfamido, $C_{1-3}$-alkoxycarbonyl, carboxyl, trifluoromethylsulfonyl, cyano, carbamoyl, sulfamoyl and acetyl, or $R_1$ represents naphthyl, $R_2$ represents hydrogen, hydroxy, $C_{1-3}$-alkoxy, acetyloxy or propionyloxy, Aa represents the group (v)

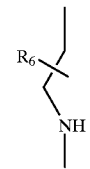

(v)

wherein $R_6$ represents hydrogen or $C_{1-3}$ unbranched alkyl, and

Prot represents a protective group.

18. A method of treating a psychiatric disorder in a human or animal patient in need of such treating, wherein the method comprises administering to the patient a compound of formula (I) as claimed in claim 1 in an amount efficacious for the treating.

19. The method of claim 18, wherein the psychiatric disorder is chosen from psychosis, anxiety, depression, an attention deficit, a memory disorder, an appetite disorder, obesity, a neurological disorder, dementia, distonia, Alzheimer's disease, epilepsy, Huntington's disease, Tourette's syndrome, ischaemia, pain, and a CNS-disease.

20. The method of claim 19, wherein the CNS disease is one involving cannabinoid neurotransmission.

21. The method of claim 19, wherein the neurological disorder is Parkinson's disease.

22. A method of treating a gastrointestinal disorder in a human or animal patient in need of such treating, comprising administering to the patient an amount of a compound of formula (I) as claimed in claim 1, wherein the amount is efficacious for the treating.

23. The method of claim 22, wherein the gastrointestinal disorder involves cannabinoid neurotransmission.

24. A method of treating a cardiovascular disorder in a human or animal patient in need of such treating, comprising administering to the patient an amount of a compound of formula (I) as claimed in claim 1, wherein the amount is efficacious for the treating.

* * * * *

UNITED STATES PATENT AND TRADEMARK OFFICE
CERTIFICATE OF CORRECTION

PATENT NO.    : 6,476,060 B2
DATED         : November 5, 2002
INVENTOR(S)   : Josephus H.M. Lange et al.

It is certified that error appears in the above-identified patent and that said Letters Patent is hereby corrected as shown below:

<u>Column 30,</u>
Claim 16, in the structure for formula (XII)

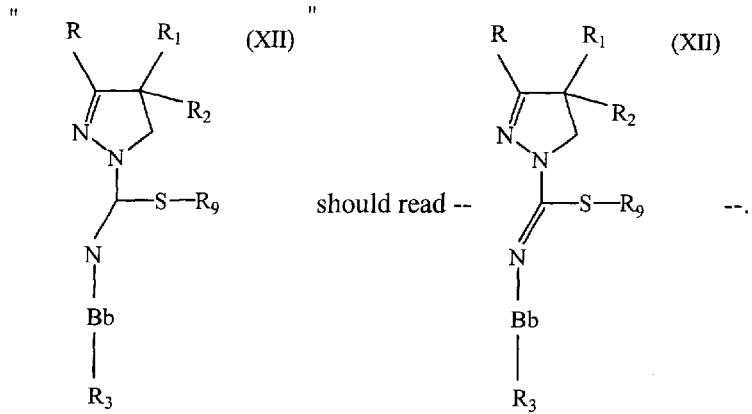

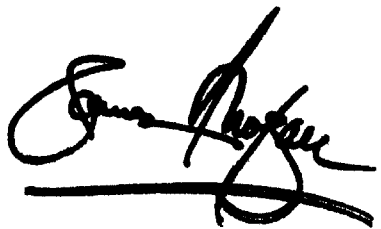

Signed and Sealed this

Eighth Day of April, 2003

JAMES E. ROGAN
*Director of the United States Patent and Trademark Office*